United States Patent [19]

Koal et al.

[11] Patent Number: 4,585,970
[45] Date of Patent: Apr. 29, 1986

[54] FLEXIBLE PIEZOELECTRIC SWITCH

[76] Inventors: Jan G. Koal; Carl V. Wells, both of NE 820 California St., Pullman, Wash. 99163

[21] Appl. No.: 710,226

[22] Filed: Mar. 11, 1985

[51] Int. Cl.⁴ .............................................. H01L 41/08
[52] U.S. Cl. .................................... 310/331; 310/339; 310/800
[58] Field of Search ................................ 310/330–332, 310/800, 339; 340/500, 573

[56] References Cited

U.S. PATENT DOCUMENTS

| | | | |
|---|---|---|---|
| 3,166,730 | 1/1965 | Brown, Jr. et al. | 310/800 X |
| 3,239,696 | 3/1966 | Burkhalter et al. | 310/331 X |
| 3,798,474 | 3/1974 | Cassand et al. | 310/800 X |
| 3,831,586 | 8/1974 | Petit | 310/330 X |
| 3,903,733 | 9/1975 | Murayama et al. | 310/800 X |
| 3,940,637 | 2/1976 | Ohigashi et al. | 310/800 X |
| 3,971,250 | 7/1976 | Taylor | 310/800 X |
| 4,051,395 | 9/1977 | Taylor | 310/800 X |
| 4,054,808 | 10/1977 | Tanaka | 310/800 X |
| 4,186,325 | 1/1980 | Gudzin | 310/331 |
| 4,191,193 | 3/1980 | Seo | 310/800 X |
| 4,443,730 | 4/1984 | Kitamura et al. | 310/800 X |
| 4,499,394 | 2/1985 | Koal | 310/800 X |

Primary Examiner—Mark O. Budd
Attorney, Agent, or Firm—Keith S. Bergman

[57] ABSTRACT

An elongate piezoelectric plastic is embodied in a flexible casement to serve as a switching element for electrically motivated apparatus especially as used by disabled persons. The ends of the switch are adhered to portions of a human body that may be moved relatively to each other for activation. The plastic piezoelectric element is of a particular compound nature to enhance signal strength and of a particular configuration to prevent noise and shorting at the peripheral edges. Ancillary electrical circuitry enhances signal strength, logically evaluates multiple signals and annunciates those signals audibly or electrically for relay activated switching of other devices.

5 Claims, 6 Drawing Figures

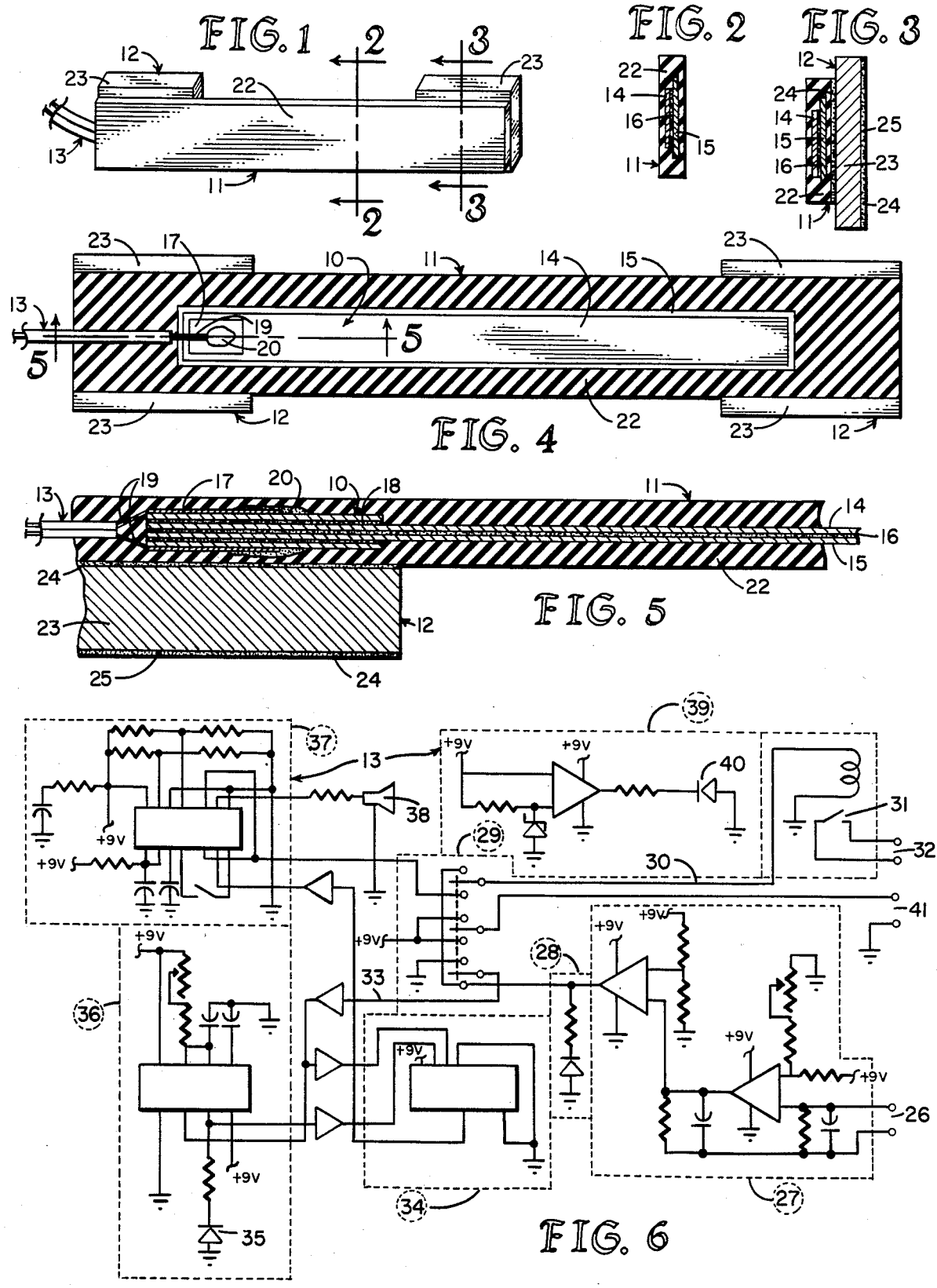

FLEXIBLE PIEZOELECTRIC SWITCH

BACKGROUND OF INVENTION

1. RELATED APPLICATIONS

There are no applications related hereto heretofore filed in this or any foreign country.

2. FIELD OF INVENTION

This invention relates generally to flexible piezoelectric switches and more particularly to such switches that may be adhered to the human body for activation by relative motion of body parts.

3. DESCRIPTION OF PRIOR ART

Since the advent of piezoelectric plastics that emit electric current responsive to impingement of some physical force, the material has been used in switching devices of various sorts. The early switch applications using this material provided configurations that sense a pressure type force. As this type of switch evolved and became more sophisticated, the configuration of the sensor was modified so that the sensing material might resiliently deform responsive to pressure as in bending or stretching. This latter type configuration has generally been found to be both more reliable and reactive than pressure sensing.

Our invention carries the evolutionary course of development of such switches further by providing a resiliently flexible sensing area that reacts entirely to flexion type deformation rather than a directly applied pressure type force. This use of deformable piezoelectric material allows our switch to provide a flexible portion suspended between two more rigid supports and this configuration allows the switch to be particularly adapted for use by handicapped persons. The support structures may be adhered to various portions of the human body which may be moved relative to each other, such as between the eyebrow and the forehead or across an arm, finger, or leg joint and may even be activated by muscle motion when the device is positioned on the surface of a large muscle or on both sides of a juncture between muscles. This particular switch configuration allows sensing material to be encapsulated but yet remain flexible and the suspension of the flexible portion between two more rigid fastening elements tends to enhance the flexion of the more deformable portion.

The electric current generated by piezoelectric plastics is quite small in absolute value and generally must be enhanced to be particularly useful in most commercial applications. Commonly, this enhancement is brought about either by forming compound sensors with plural elements that have additive electric functions, by amplifying the electric output of a sensor with one or more amplifying devices, or by the combination of both such methods.

Our invention uses both methods of signal enhancement to provide a switch that is of high sensibility and substantial reliability but yet with low maintenance. In the past, compound plastic piezoelectric switching elements have been difficult of formation and not of high reliability. These problems generally have arisen from the sensor formation process itself, wherein the edges of various plastic elements must be cut or severed. In this process the conductive surface coatings of the elements may be physically moved or the plastic body carrying them may be deformed so that the conductive surfaces on opposite sides of a piezoelectric sensor may come close to each other or into actual physical contact. The formation process also tends to leave some irregularities in the peripheral edges of the sensor which, if they be not sufficient to cause direct shorting, may cause extraneous electrical noise during use.

Our invention solves these problems by providing a compound sensor of the stacked type formed of elements of similar shape but different size so that the peripheral edges of adjacent elements are not coincident. This configuration tends to do away with, or at least substantially reduce, any shorting of the piezoelectric elements and any excessive noise being generated by their motion. Again, in the traditional compounding of plastic piezoelectric sensors, the elements have been arrayed or interconnected in a serial fashion which maintains the positive side of one element adjacent the negative side of an adjacent element. We have found that better results are had and greater output obtained, with more reliability and less noise, when two sensors are related in a parallel fashion with adjacent sides both of the same polarity. Two adjacent negative elements are not directly electrically interconnected but rather maintained in spaced adjacency by a non-conductive adhesive carried between the two surfaces to provide a very small insulative gap. Such sensors have been found to have superior output and very low noise generation.

Our sensor structure allows encapsulation by known methods and may be serviced by most electronic sensing, annunciating and amplifying devices that have heretofore been used with such devices.

A particular control device associated with our piezoelectric switch provides an amplifier to enhance sensor current and operate visual and optical annunciators and a relay activated switch for operation of other electrical circuits. The control device has logic circuits including counting and timing devices to require a predetermined number of sensor pulses at predetermined timed intervals as a threshold for activation to avoid any accidental or unwanted activation of the switch. The circuitry also allows direct connection to a relay, should this be desired.

Our invention resides not in any one of these structural features or functions per se, but rather in the particular synergistic combination of all of them disclosed, specified and claimed herein.

SUMMARY OF INVENTION

Our invention generally provides an elongate encapsulated plastic piezoelectric sensing element supported in its end parts for attachment to a human body and having associated electrical circuitry to cause annunciation responsive to sensor flexion.

Our sensing element provides two similar sheet-like piezoelectric plastic elements having their negative surfaces in adjacency and attached by insulating adhesive. The sensor is encapsulated by flexible protective material supported at its end parts by more rigid fastening elements that are attached to spaced portions of a human body which may be relatively moved. The stacked piezoelectric elements are of similar shape but different size and so arrayed that their peripheries do not form a coplanar configuration, all to avoid shorting between opposed conductive surfaces and undue electrical noise.

Associated electrical circuitry amplifies switch output and translates the amplified output into auditory, visual and physical annunciation, to provide information to third parties and activation to secondary devices.

In creating such a device, it is:

A principal object of our invention to provide a piezoelectric switching sensor that operates by flexion so that it may be supported by its end parts on a human body and activated by motion of the supporting body parts relative to each other.

A further object of our invention to provide such a device that has a compound piezoelectric sensing element formed by two sensors having similarly charged surfaces in spaced adjacency and interconnected by electrically insulative adhesive.

A further object of our invention to provide such a device that has piezoelectric elements of similar shape but different size, so arrayed that their peripheries are not coincident, to prevent shorting and reduce electrical noise.

A further object of our invention to provide such a device that may be encapsulated in a flexible protective cover and supported by more rigid spaced supports in its end parts to aid flexion of the medial, more resilient part of the device.

A still further object of our invention to provide associated electrical circuitry for such a device that amplifies its signal and uses that signal to cause responsive visual, auditory and physical annunciation to third parties and secondary devices.

A still further object of our invention to provide associated logic circuitry that requires certain patterns of signals, both as to number and interval, for annunciation to prevent accidental activation.

A still further object of our invention to provide such a device that is of new and novel design, of rugged and durable nature, of simple and economic manufacture and one otherwise well suited to the uses and purposes for which it is intended.

Other and further objects of our invention will appear from the following specifications and accompanying drawings which form a part hereof. In carrying out the objects of our invention, however, it is to be understood that its essential features are susceptible of change in design and structural arrangement with only one preferred and practical embodiment being illustrated in the accompanying drawings as is required.

BRIEF DESCRIPTION OF DRAWINGS

In the accompanying drawings, which form a part hereof and wherein like numbers of reference refer to similar parts throughout;

FIG. 1 is an isometric surface view of the sensor element of our invention showing its various parts, their configuration and relationship.

FIG. 2 is an enlarged cross-section view through the medial portion of the sensor of FIG. 1, taken on the line 2—2 thereon in the direction indicated by the arrows.

FIG. 3 is an enlarged cross-sectional view of the end part of the sensor of FIG. 1, taken on a line 3—3 thereon in the direction indicated by the arrows.

FIG. 4 is an enlarged and cutaway view of the sensor of FIG. 1 having the surface encapsulation removed to show the switching element per se.

FIG. 5 is a partial elongate, enlarged cross-sectional view of the switch of FIG. 4, taken on the line 5—5 thereon in the direction indicated by the arrows.

FIG. 6 is an electrical diagram, in normal symbology, of the circuitry associated with our switching device, with various functional portions identified in dotted outline for ease of understanding and description.

DESCRIPTION OF THE PREFERRED EMBODIMENT

Our invention generally provides plastic piezoelectric sensing member 10, protected by flexible encapsulation member 11 which carries spaced supports 12 at its end parts, and associated electrical circuitry 13 for signal amplification and annunciation.

Sensing member 10 is formed by two elongate flexible polymeric piezoelectric elements 14, 15 both of similar shape but with one element 14 slightly smaller than the second element 15. These piezoelectric elements are arrayed in symmetric stacked fashion. By reason of their different size and array, the peripheral edges of the two elements will not be coincident. These elements are normally formed from a larger piece of polymeric material by some type of shearing or cutting action. This action often leaves roughness about the peripheral edges of the elements, causes deformation of a permanent or semi-permanent nature in the peripheral area or both. These irregularities often create electrical noise when the elements are used or may even cause shorting of a temporary or permanent nature between conductive portions of adjacent sensing elements. The difference in size of the elements in our invention tends to prevent or substantially alleviate these problems.

The two sensing elements are arranged in a stacked array as shown especially in the illustration of FIG. 4. The elements are so positioned as to have their negative surfaces adjacent each other and are physically interconnected with electrically non-conductive adhesive 16 forming a continuous membranous-like coating therebetween. The negative surfaces of the two sensing elements must be in fairly immediate adjacency for this array of elements to be operative so the layer of insulating adhesive 16 must be relatively thin, generally in the order of three to five thousandths of an inch, but yet that layer must be continuous to prevent any direct electrical contact between the conductive surfaces of the two sensing elements.

The particular shape and size of the sensing elements is not critical to our invention, but preferably it will be in the range of 0.5 inches in width and 3.0 inches in length for normal use on a human body. The particular material from which the sensing elements are formed is one of the polyvinylidene fluoride compounds such as that known as "kynar", as manufactured and merchandised by Pennwalt Chemicals. Undoubtedly other similar piezoelectric polymers that generate a voltage upon flexion would be operative with our switch, if possibly not so effectively. These films provide a thin, tough polymeric sheet with conductive surface coatings that emit a voltage of a few tenths of a volt upon activation.

Such polymeric piezoelectric elements are interconnected into electrical circuitry with some difficulty and generally specialized connecting devices are required, especially such as shown in FIG. 4. Here conductive metallic foil patches 17, in the instant device formed of copper, are interconnected to each of the outer positive surfaces of the two stacked sensing elements. These metallic foil patches, of the rectilinear shape illustrated and with a width somewhat less than the width of the smaller sensing element, provide a contacting surface of some area. The strips are adhered to the conductive surface of the sensing elements by electrically conductive adhesive 18. They are by their positioning electrically isolated from each other. Each patch is configured and positioned so as to leave a border between its periphery and that of the underlying sensor element so as to avoid any possibility of electrical shorting at the periphery of the sensors. The outer portion of each foil strip, inwardly adjacent the end part, is interconnected with output wires 19 by conductive adhesion, as by soldering 20. Normally piezoelectric sensing elements may not effectively be directly interconnected with output wires because of the difficulty of forming an electrically interconnecting bond, the physical damage that might be done by the wires to the sensing elements especially as enhanced by any flexion of either element, and the electric noise generated by such an interconnection.

Encapsulation member 11 provides electrically insulative polymeric material 22 of a sheet-like nature extending about the sensing element to completely cover it. The encapsulating material provides both physical and electrical protection for the sensing element but must be sufficiently deformable to allow that element to flex without any substantial hindrance. The exact configuration and dimensioning of the encapsulating material is not critical, but preferably its periphery is of the elongate rectilinear shape illustrated, with a length several times its width and overall length approximately thirty percent longer than the length of sensing elements. Normally the encapsulating material will comprise one of the neoprene polymers or something similar. It may be established about the sensing element by molding, adhesion or other similar processes well known in the plastic arts.

Support structures 12 comprise semi-rigid supports 23, less deformable than the encapsulation member, carried on the same side of the encapsulating member 11 at each of its end parts. The exact shape and configuration of supports 23 is not particularly critical, but they normally will be formed of foamed polymeric material somewhat wider and somewhat thicker than the encapsulation member to properly position the sensing element and assure that the supports have somewhat greater rigidity. The supports extend inwardly sufficiently to provide a surface of some substantial area to allow connection with the encapsulation material and a human body, but yet leave a substantial space between the supports where the medial switch portion may flex. Normally in a sensing device having an elongate dimension of approximately three inches, these supports should have an elongate dimension of approximately one-half inch. Again, preferably but not necessarily, the dimensioning and arrangement of output wires 19 and metallic foil strip 17 is such that the interconnections occur adjacent one of the supports so that this interconnection will not flex so readily as if the area were located between supports.

Each support 23 is mechanically interconnected to the adjacent surface of the encapsulating member by adhesion, with adhesive film 24 communicating therebetween. This adhesive is such as to create a releasable bond that allows the adhered elements to be separated if desired. The outer surface 25 of each support, that is the one most distal from the encapsulation, is provided with a similar layer of adhesive to releasably bond with the skin of a human. This later adhesive must adhere to human skin but yet release therefrom without causing damage and must not irritate or harm the skin to which it adheres. The common latex-type adhesives or adhesives used on surgical tapes are quite well adapted for this purpose. Generally both adhesive layers carried by the supports are of the same type, so that either adhered element may be removed without damaging the surface to which it is adhered.

Electrical circuitry 13, of a type commonly used with our sensor, is illustrated in normal symbology in FIG. 6 of the drawings, wherein various functional units of the circuitry are indicated in dotted outline to aid understanding.

In the circuitry, the output of sensing device 10 is input through leads 26 from which the signal passes to comparator 27 which compares the input signal magnitude to a voltage reference and outputs a signal when the input voltage exceeds the reference voltage. The output signal then passes to activate indicator light circuitry 28 to annunciate the input and thence through switch 29 which allows selection of various other annunciative functions such as to activate a relay or an audible annunciator. The relay circuitry passes through leads 30 to relay switch 31 from whence the output is taken off through connectors 32 to operate separate circuitry (not shown).

Buzzer output from switch 29 passes through lead 33 to counting circuit 34 which requires a certain number of successive input signals for activation, each of which is indicated by indicator light circuit 28. The signal passes conditionally, if the input limitations are met, to timing circuitry 36 which requires a predetermined number of input signals to be presented within a predetermined time interval. If this condition be met, the event is annunciated by light 35 and current is passed to timing circuit 37 which activates buzzer-type annunciator 38 to provide an audible response upon receipt of an appropriate signal.

Battery tester 39 is provided to annunciate through indicator light 40 to visually indicate battery condition of the device, which is powered by an ordinary nine volt storage battery (not shown).

Though specific electronic circuitry is shown in the diagram of FIG. 6, obviously the functions described may be accomplished by many and various circuits other than those shown. The circuitry is not new per se and is not essential in any particular form to the operation of our sensor, though normally some amplification of a signal must be accomplished before it may be readily used. Other electrical circuits heretofore known may well serve the ends of our invention.

Having thusly described our invention, its operation may be understood.

Firstly, a switch is constructed according to the foregoing specifications and interconnected with appropriate electrical circuitry, such as that described, to make use of its electrical output.

Normally after manufacture, adhesive on the outer surfaces of supports 23 is covered by some protective membrane, and if this be the case, the membrane is removed to expose the adhesive and render it ready for use. The switch is then manually manipulated to position it, with some pressure, on two spaced portions of the human body that may be moved voluntarily relatively to each other to cause some flexion in the sensing element extending between the supports. This positioning may be accomplished such as over the skin adjacent an eye, the skin adjacent the mouth, the skin adjacent various joints in fingers or toes or elsewhere on the body where spaced portions may be relatively moved. The movement required actually is quite slight, as the switch is most sensitive and its sensitivity may be regulated by appropriate amplification of its signal. The switch may be adhered to the body at the desired position by manual pressure on the encapsulation material adjacent the support elements to cause the adhesive carried by a support to adhere to the skin. Normally once adhered the device will remain in place for substantial periods of time and generally until manually removed. The adhesive attachment of supports to the encapsulation member allows support replacement when required especially as for sanitary reasons.

Once the switch is so positioned, the portion of the body involved may be appropriately moved to cause some flexion in the encapsulation member embodying the switching element. When this occurs, an electric current will be generated by reason of the piezoelectric activity of the sensor element, principally because of the stretching or stressing of its structure. The signal is received by the associated electric circuitry, amplified and put to use thereby either in activating a switching relay or operating some sort of annunciator.

The switch, after its use be completed, may be removed by ordinary manual manipulation. Preferably, an adhered surface is rather rolled from the skin, the sensor covering, or both to avoid and severe stressing or stretching of the sensing element which could cause permanent damage to it and cause it to lose its sensitivity. Our switches normally may be used for long periods of time, if not indefinitely, so long as they are not physically damaged by external forces.

The foregoing description of our invention is necessarily of a detailed nature so that a specific embodiment of it might be set forth as required, but it is to be understood that various modifications of detail, rearrangement and multiplication of parts may be resorted to without departing from its spirit, essence or scope.

Having thusly described our invention, what we desire to protect by Letters Patent and

What we claim is:

1. A flexible polymeric piezoelectric switching device, for use on a human body, to be activated by relative motion of two spaced portions of the body relative to each other, comprising, in combination:
    a sensing element having at least two similarly configured, sheet-like polymeric piezoelectric sensors in stacked array with electric interconnection to enhance the output of the combined sensors,
        said sensors being of different sizes and arrayed so that no peripheral edges are coincident with each other and;
        the adjacent sides of the sensors being adhered to each other by relatively thin, adhesive and;
    connecting circuitry including electrically conductive metallic foils having substantial surface contact with the outer surfaces of each of the piezoelectric elements at spaced distance inwardly of the periphery thereof,
        the adjacent surfaces of the metallic foils and piezoelectric elements being adhered by electrically conductive adhesive and
        said foils having electrically conductive wires interconnected thereto, and extending away therefrom, by an electrically conductive fastening means;
    an encapsulation member surrounding the arrayed sensing elements and connecting circuitry with the interconnecting wires extending therefrom; and
    supports carried at opposite end parts of the encapsulation member and extending inwardly toward each other to a spaced distance, each of said supports having adhesive on their outer surfaces opposite their interconnection with the encapsulation member to releasably adhere to the surface of a human body.

2. The invention of claim 1 further characterized by:
    the piezoelectric sensors having similarly charged surfaces in spaced adjacency and
    a thin layer of electrically insulative adhesive interconnecting the adjacent surfaces of the piezoelectric sensors.

3. A flexible piezoelectric switch, for activation by relative movement of closely spaced portions of a human body, comprising, in combination:
    a sensing member having two sheet-like polymeric piezoelectric elements in stacked array with negative sides adjacent and adhered to each other by a thin continuous film of an electrically insulative adhesive, the first piezoelectric element being of similar shape to the second but of smaller size and said elements arrayed so that their peripheries are not anywhere coincident;
    electric connecting circuitry, communicating with the outer positive sides of the sensing elements, comprising electrically conductive metallic foils adhered to the conductive surfaces of the opposed outer sides of the piezoelectric sensors, at a spaced distance inwardly from their peripheries, with electrically conductive adhesive, said metallic foils having electrically conductive connecting wires fastened to their outer surfaces by electrically conductive means;
    an elongate encapsulation member enclosing said piezoelectric sensing elements and the associated electric connecting circuitry with the conductive connecting wires extending therefrom;
    semi-rigid supports structurally communicating with the end parts of said encapsulation member and extending inwardly to a spaced distance from each other, said supports having adhesive on their outer surfaces opposite their interconnection with the encapsulation member to releasably adhere to a human body; and
    associated electric circuitry adapted to amplify a signal produced by said sensing elments and annunciate that signal upon predetermined conditions.

4. The invention of claim 3 wherein at least a substantial portion of the piezoelectric sensing element is carried in the encapsulation member between the supports and the interconnection of conductive wires with metallic foils is adjacent the interconnection of a support with the encapsulation.

5. A method of communication for disabled persons, comprising in combination:
    the attachment of a flexible switching device to spaced portions of the human body that may be voluntarily moved relative to each other, said sensing device having
        a sensing element with two similarly configured, slightly differently sized piezoelectric sensors arrayed in stacked relationship with negative sides in spaced adjacency and with non-coincident peripheral edges
        said sensors being adhered to each other with electrically non-conductive adhesive and
        covered by a flexible elongate encapsulation member having spaced semi-rigid supports in its end parts for releasable attachment to spaced, relatively movable portions of a human body;

connecting circuitry communicating with the sensing element to transmit an electrical signal therefrom to associated electrical circuitry that amplifies and annunciates the electrical signal presented upon the fulfillment of predetermined conditions; and voluntary relative motion of the two portions of a human body to which the sensing device is attached to cause the sensing device to generate an electrical signal.

* * * * *